(12) United States Patent
Werner et al.

(10) Patent No.: US 11,191,456 B2
(45) Date of Patent: Dec. 7, 2021

(54) ON-DEMAND TESTING FOR SELECTED CONDITIONS

(71) Applicant: INTERNATIONAL BUSINESS MACHINES CORPORATION, Armonk, NY (US)

(72) Inventors: John S. Werner, Fishkill, NY (US); Byron S. Green, Poughkeepsie, NY (US); William L. Brodsky, Binghamton, NY (US); Robert K. Mullady, Ulster, NY (US); Jeffrey A. Newcomer, Poughkeepsie, NY (US); Arkadiy O. Tsfasman, Wappingers Falls, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 488 days.

(21) Appl. No.: 16/201,163

(22) Filed: Nov. 27, 2018

(65) Prior Publication Data
US 2020/0163592 A1 May 28, 2020

(51) Int. Cl.
*A61B 5/12* (2006.01)
*A61B 5/00* (2006.01)
(Continued)

(52) U.S. Cl.
CPC ............ *A61B 5/125* (2013.01); *A61B 5/6803* (2013.01); *A61B 5/746* (2013.01); *A61F 11/14* (2013.01);
(Continued)

(58) Field of Classification Search
CPC ................ H04R 1/1083; H04R 1/1041; H04R 2420/07; H04R 29/001; H04R 29/008;
(Continued)

(56) References Cited

U.S. PATENT DOCUMENTS

2008/0137873 A1* 6/2008 Goldstein ............ H04R 1/1083
381/57
2014/0243702 A1 8/2014 Levine
(Continued)

FOREIGN PATENT DOCUMENTS

WO WO2012014175 A1 2/2012

OTHER PUBLICATIONS

Mell, Peter and Tim Grance, "The NIST Definition of Cloud Computing," National Institute of Standards and Technology, Information Technology Laboratory, Special Publication 800-145, Sep. 2011, pp. 1-7.
(Continued)

*Primary Examiner* — Lun-See Lao
(74) *Attorney, Agent, or Firm* — Tihon Poltavets, Esq.; Kevin P. Radigan, Esq.; Heslin Rothenberg Farley & Mesiti P.C.

(57) ABSTRACT

A device is used to monitor, in real-time, one or more environment conditions of an environment in which a user is located. Based on the monitoring, an alert condition relating to the environment is detected. Based on detecting the alert condition, on-demand testing of a sensory component of the user is initiated. The on-demand testing tests for a selected condition relating to the health of the user.

20 Claims, 10 Drawing Sheets

(51) Int. Cl.
    *A61F 11/14* (2006.01)
    *H04R 1/10* (2006.01)
    *H04R 29/00* (2006.01)
(52) U.S. Cl.
    CPC ......... *H04R 1/1008* (2013.01); *H04R 1/1083* (2013.01); *H04R 29/001* (2013.01); *A61B 2560/0242* (2013.01); *H04R 2420/07* (2013.01)
(58) Field of Classification Search
    CPC .............. H04R 1/1016; H04R 2410/05; H04R 2430/03; H04R 2460/15; H04R 29/00; H04R 3/002; H04R 1/1091; H04R 2225/025; H04R 25/353; H04R 25/356; H04R 2225/39; H04R 2225/41; H04R 2225/55; H04R 2430/01; H04R 2460/01; H04R 25/305; H04R 25/505; H04R 1/028; H04R 2205/041; H04R 2460/07; H04R 25/70; H04R 25/75; H04R 3/04; H04R 5/04; H04R 19/005; H04R 19/04; H04R 1/1008; H04R 1/406; H04R 2201/003; H04R 2201/405; H04R 2499/13; H04R 25/50; H04R 25/554; H04R 25/558; H04R 29/002; H04R 3/005; A61B 8/06; A61B 8/0808; A61B 8/488; A61B 8/565; A61F 11/08; A61F 11/06; A61F 2011/145; A61F 11/14; H04L 63/0236; H04L 63/101; H04L 63/168; H04L 67/02; H04L 43/50; H04L 65/60; H04L 41/0886; H04L 41/5019; H04L 41/5038; H04L 29/06176; H04L 41/0604; H04L 43/065; H04L 43/0811; H04L 43/10; H04L 51/04; H04L 65/4084; H04L 65/4092; H04L 65/601; H04L 67/104; H04L 67/18; H04L 67/306; H04B 1/385; H04B 2001/3855; H04B 5/06; H04B 1/1036; H04W 4/023; H04W 4/029; H04W 4/02; H04W 4/025; H04W 4/00; H04W 84/18; G10L 15/04; G10L 15/26; G10L 17/26; G10L 25/00; G10L 15/22; G10L 21/0208
    USPC .......................... 381/60, 312, 323; 600/599
    See application file for complete search history.

(56) References Cited

U.S. PATENT DOCUMENTS

| | | | |
|---|---|---|---|
| 2016/0234606 A1* | 8/2016 | Selig | H04R 25/70 |
| 2016/0249835 A1 | 9/2016 | Zhao et al. | |
| 2016/0302012 A1 | 10/2016 | Sprague et al. | |
| 2016/0374595 A1* | 12/2016 | Henriksen | A61F 11/08 |
| | | | 600/559 |
| 2017/0047059 A1 | 2/2017 | Yang et al. | |
| 2017/0150282 A1 | 5/2017 | Mishra et al. | |
| 2018/0035216 A1* | 2/2018 | Van Hasselt | A61B 5/6898 |
| 2018/0089976 A1* | 3/2018 | Yarlagadda | G06Q 10/063118 |

OTHER PUBLICATIONS

Buckey, Jay et al., "Pure-tone Audiometric Threshold Assessment with In-Ear Monitoring of Noise Levels," Int J Audiol, Author Manuscript, PMC Jun. 28, 2016, pp. 1-17.

* cited by examiner

ON-DEMAND TESTING FOR SELECTED CONDITIONS

BACKGROUND

One or more aspects relate, in general, to testing for selected conditions, and in particular, to on-demand testing for the selected conditions.

There are many different conditions for which tests may be performed. Often, the tests are performed at static points in time, and thus, the information is limited, or responses may be delayed. The information may be obtained too late to prevent damage, injury or loss.

SUMMARY

Shortcomings of the prior art are overcome, and additional advantages are provided through the provision of a method of facilitating testing. A device is used to monitor, in real-time, one or more environment conditions of an environment in which a user is located. Based on the monitoring, an alert condition relating to the environment is detected. Based on detecting the alert condition, on-demand testing of a sensory component of the user is initiated. The on-demand testing tests for a selected condition relating to the health of the user.

Devices, systems and computer program products relating to one or more aspects are also described and may be claimed herein. Further, services relating to one or more aspects are also described and may be claimed herein.

Additional features and advantages are realized through the techniques described herein. Other embodiments and aspects are described in detail herein and are considered a part of the claimed aspects.

BRIEF DESCRIPTION OF THE DRAWINGS

One or more aspects are particularly pointed out and distinctly claimed as examples in the claims at the conclusion of the specification. The foregoing and objects, features, and advantages of one or more aspects are apparent from the following detailed description taken in conjunction with the accompanying drawings in which:

DETAILED DESCRIPTION

Figure 1:
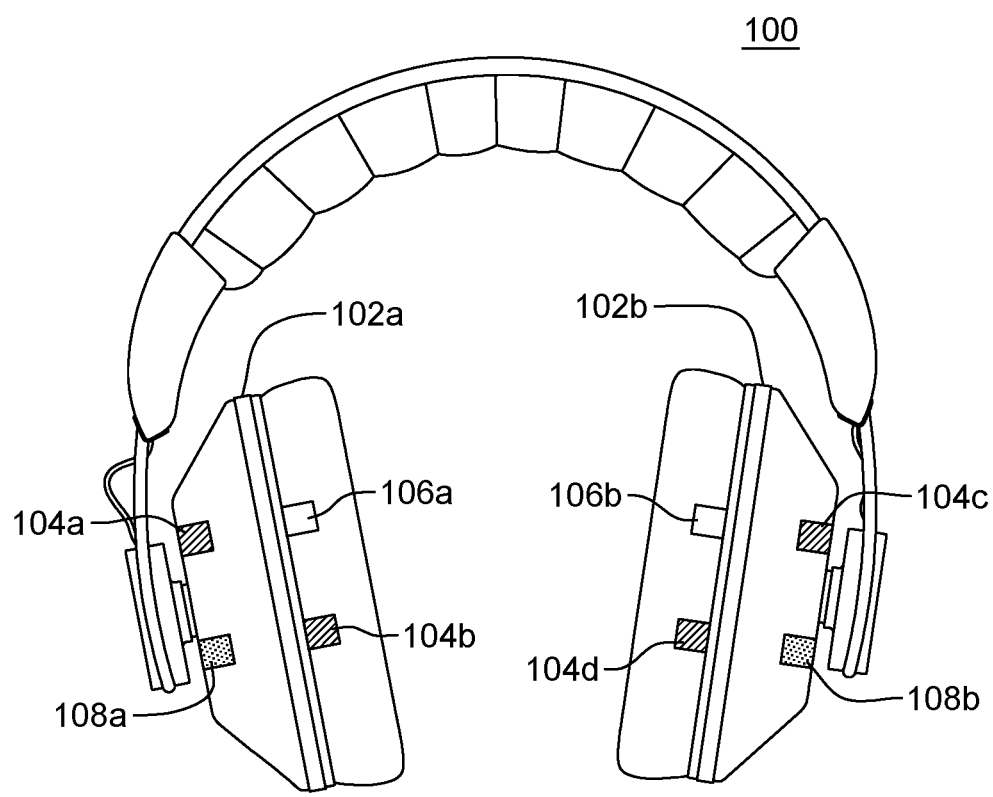
FIG. 1 depicts one example of a hearing protection device to incorporate and/or use one or more aspects of the present invention.

In accordance with one or more aspects, on-demand testing for selected conditions is provided. The on-demand testing employs, for instance, wearable technology, including internet-of-things wearable technology, and/or cognitive analysis. The testing may be performed in real-time to determine if a selected condition exists. As examples, the selected conditions are health or safety conditions of a user (e.g., a person). As used herein, on-demand testing is testing that is to be performed at the time the user is notified that testing is to be performed. It is not, for instance, routine testing that is scheduled for some particular date and time, but rather testing that is initiated by a real-time condition.

One example of a selected condition is a condition relating to hearing, such as hearing loss. In one aspect, on-demand testing is performed to determine if a user is at risk of injury, such as hearing loss or potential hearing loss, based on real-time conditions. Real-time conditions are current conditions, such as current noise level. Although the examples described herein relate to hearing and noise levels, one or more aspects may pertain to other selected conditions.

As is known, users that are exposed to high sound levels may experience noise induced hearing loss, which is hearing impairment resulting from exposure to high decibel (dB) sound that may exhibit as: a loss of a narrow range of frequencies, impaired cognitive perception of sound, and/or other impairments including hyperacusis or tinnitus. Hearing may deteriorate gradually from chronic and repeated noise exposure or suddenly, from an acute, high intensity noise incident.

Example decibel levels and associated hearing damage are provided below:

| dB Level | When Hearing Damage Occurs |
| --- | --- |
| <85 | No damage |
| 95 | After 4 hours of exposure per day |
| 100 | After 2 hours of exposure per day |
| 105 | After 1 hour of exposure per day |
| 110 | After 30 minutes of exposure per day |
| 115 | After 15 minutes of exposure per day |
| 120 | Almost immediately |

In accordance with an aspect of the present invention, a capability is provided to initiate on-demand hearing tests based on one or more alert conditions detected in real-time. For instance, an on-demand hearing test is initiated based on detecting that the user is being exposed to damaging noise levels (e.g., the current environment is too loud). Based on the detected condition, in one example, the user is notified to remove themselves from the environment and to perform a hearing test at that time.

In one example, to detect the condition and/or to perform the on-demand test, a device is employed. The device is, in one example, wearable technology, such as internet-of-things wearable technology. For instance, to detect potential or actual hearing loss, the wearable technology is a hearing protection device, such as headphones, ear muffs, earbuds, canal caps, ear plugs or other types of in-ear or over-the-ear hearing protection. One example of a hearing protection device is described with reference to FIG. 1.

Referring to FIG. 1, in one example, the hearing protection device is headphones 100. Headphones 100 include a first ear component 102a and a second ear component 102b. First ear component 102a includes, for instance, one or more outer microphones 104a, one or more inner microphones 104b, one or more speakers (e.g., inner speakers) 106a, and one or more sensors 108a. Similarly, second ear component 102b includes, for instance, one or more outer microphones 104c, one or more inner microphones 104d, one or more speakers (e.g., inner speakers) 106b, and one or more sensors 108b. In one example, the hearing protection device is battery powered.

In other embodiments, additional, fewer and/or other components may be used. For instance, in one embodiment, the sensors are not used. Other examples are possible. Further, the components may be placed in locations other than that shown in FIG. 1.

Figure 2:
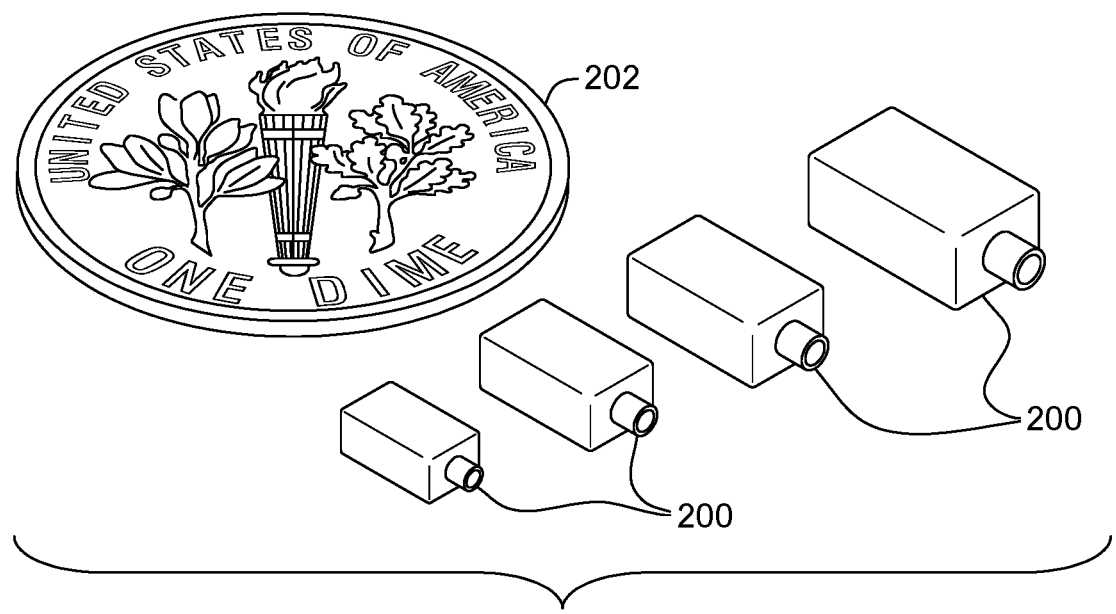
FIG. 2 depicts examples of microphones that may be used in the hearing protection device of FIG. 1, in accordance with an aspect of the present invention.

Microphones 104a-104d are, in one example, similar to those used in hearing aids, examples of which are depicted in FIG. 2. Shown in FIG. 2 are a plurality of microphones 200 of various sizes, each of which is relatively small as can be seen when compared to a coin 202. The microphones are placed, for instance, on the inside and outside of the hearing protection device, as shown in FIG. 1. In one example, sound levels on both the inner and outer microphones are monitored. The outside and inside microphones communicate with one another to ensure, for instance, that the user is wearing their hearing protection when needed (i.e., a known decibel drop should be observed based on the headphone design when a proper seal is made over the user's ears) and for general monitoring purposes.

Speakers 106a, 106b are, for instance, small speakers, such as speakers used in earbuds, that are placed, for instance, inside the hearing protection device, as shown in FIG. 1. They are used, in one embodiment, to perform standard hearing test sounds. Optionally, in one embodiment, they are used to relay audio notifications to the user.

As examples, sensors 108a, 108b are pressure, capacitive, or other sensors. A user can interact with the sensors located on the outside of the hearing protection device to perform a hearing test. For example, the user can touch the left sensor to indicate hearing a sound from the left speaker. Similarly, the user can touch the right sensor to indicate hearing a sound from the right speaker. Alternatively, a mobile device or other device can be used instead of sensors to select when and in which ear the sounds are heard.

The results of a hearing test can be used to determine, for instance, if the user is experiencing hearing loss, if the environment is the main cause of hearing loss, and/or if higher attenuation hearing protection is desirable. Other examples are possible.

In one aspect, a sound and/or notification informs the user to conduct a hearing test, on-demand. That is, the test is to be conducted at the beginning, end, or at any point during a selected limited time period, such as a work shift in a potentially noisy environment. The test may be performed by the same device that is monitoring for alert conditions. In one embodiment, if a user ignores multiple notifications (e.g., the user may be experiencing temporary hearing loss and is unable to hear the notification), a selected subject (such as a person, robot, animal) may be notified.

The test is performed in a location that is suitable, e.g., quiet enough, to perform the test. In one example, the microphones of the hearing protection device are used to determine whether the location is suitable. In one example, the test is prevented from starting until a suitable location is found. Further, in one example, the hearing test is integrated into the hearing protection device, which saves time by not having to travel to another location (other than a quieter location) to perform the test.

Figure 3:
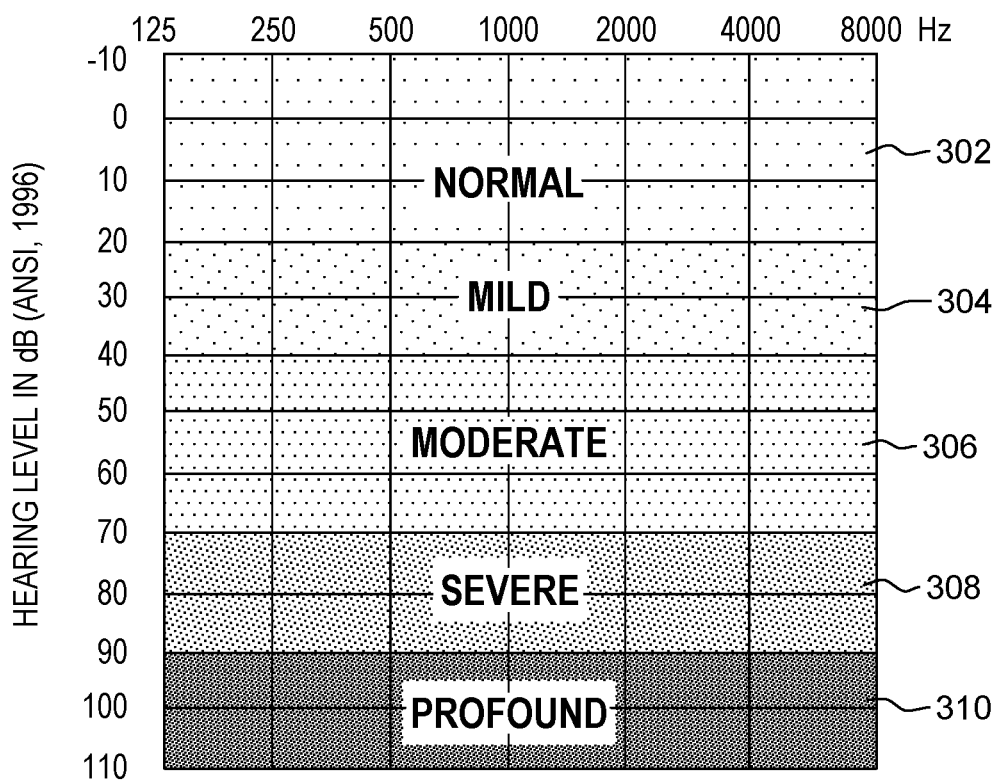
FIG. 3 depicts one example of audiogram ranges used in accordance with an aspect of the present invention.

Based on completing the test, in one aspect, an audiogram is generated and stored along with a timestamp on a user profile and/or a company database. This is used, in one embodiment, to track a user's tests in order to record the user's hearing over time. Referring to FIG. 3, an audiogram 300 displays, for instance, the softest sounds an individual can hear at different pitches and frequencies. If the sounds are in the normal range 302, then the user can hear a normal conversation; in the mild range 304, the user can hear a normal conversation in a quiet area but has difficulty in a noisy environment; in the moderate range 306, the user has difficulty hearing a normal conversation in a quiet room; in the severe range 308, the user is unable to hear a conversation unless the speaker is shouting next to the ear; and in the profound range 310, the user is unable to understand the conversation even if the speaker is shouting. Results of testing both ears may be shown in an audiogram, in which one graphical line is for one ear and another graphical line is for another ear.

In one embodiment, results are tracked over time such that a slow degrade in hearing may be detected that might not be observed from a single test.

In a further aspect, pressure data (from, e.g., pressure transducers in the microphones) is stored, along with the audiogram, for additional data that can be used to monitor and analyze hearing loss. Samples can be taken periodically for potential savings on the amount of data transmitted and stored.

If the results of the test are negative (e.g., hearing loss is detected), notifications indicate whether action is to be taken including, for instance, notifying a subject (e.g., a selected person, management, etc.); advising the individual to leave/not enter the noisy environment; and/or recommending a different form of hearing protection (e.g., higher attenuation). Other examples are possible.

If the results of the test are positive, then the user can continue in the environment (e.g., working, listening, etc.) using the hearing protection device. In one example, feedback can include how well the hearing protection device maintains its specified attenuation over time so that a user can know if their hearing protection device is degrading and should be replaced.

Figure 4C:
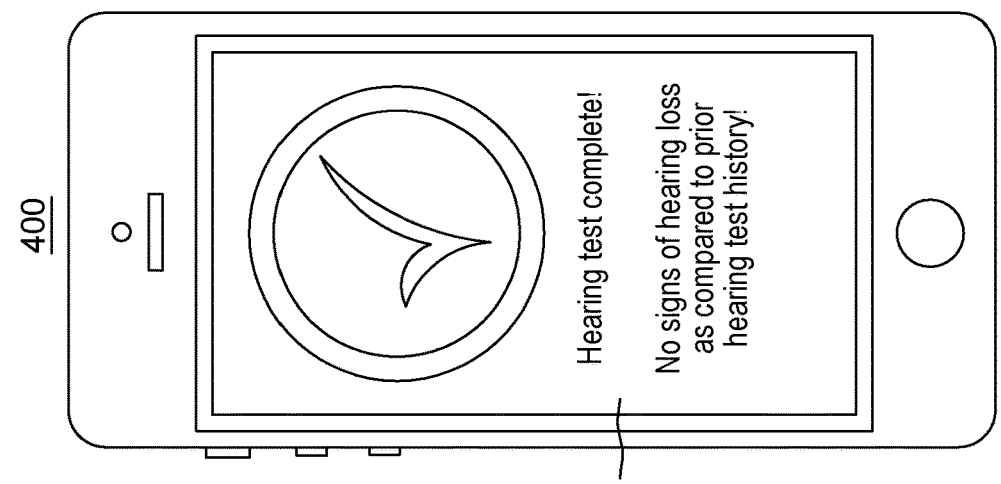
FIG. 4C depicts one example of a notification provided to the user based on performing a test, in accordance with an aspect of the present invention.
Figure 4B:
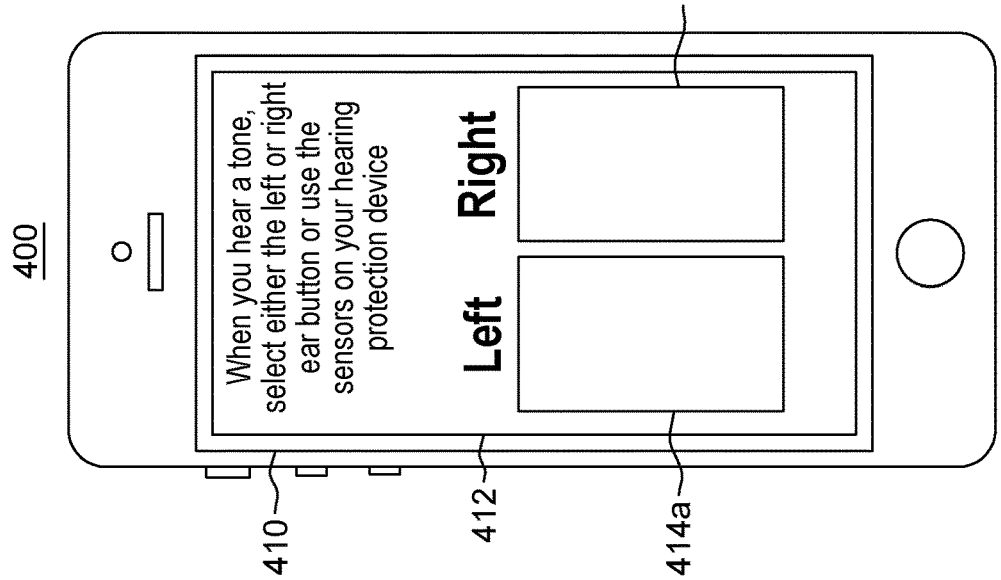
FIG. 4B depicts one example of an auxiliary device used in performing a test based on a detected condition, in accordance with an aspect of the present invention.
Figure 4A:
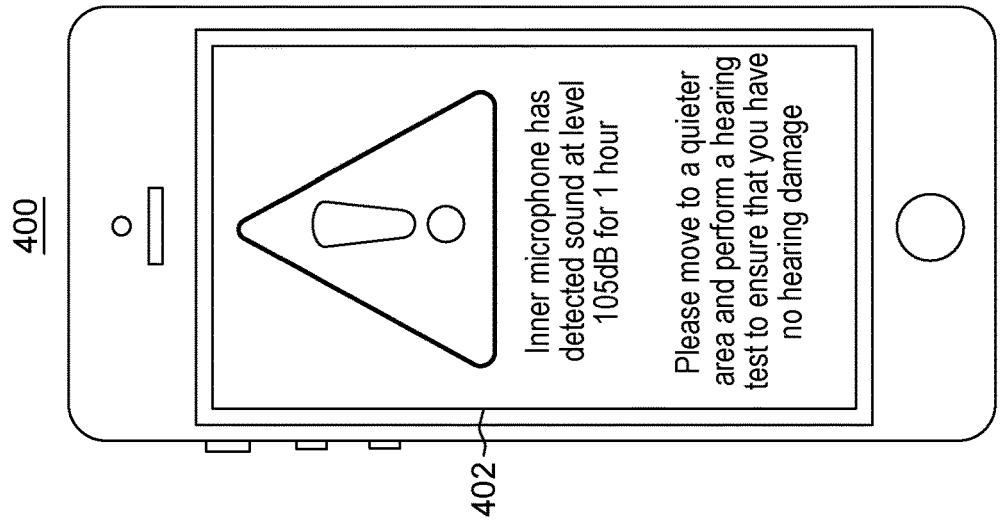
FIG. 4A depicts one example of an alert provided to a user regarding a detected condition, in accordance with an aspect of the present invention.

In one aspect, the hearing protection device contains a wireless transmitter (e.g., Bluetooth, Wi-Fi, etc.) to communicate with another device of a user, such as a mobile device, a wearable device (e.g., a watch), a tablet, etc. The hearing protection device has, e.g., an associated application (app) on the other device that may be used to instruct the user to perform a hearing test and/or to provide results, etc. As shown in FIG. 4A, in one example, the other device is a mobile device 400 that receives a notification 402 instructing the user to perform a hearing test. Further, in one example, as shown in FIG. 4B, mobile device 400 is used in performing the test. For instance, an app 410 on mobile device 400 prompts the user with a notification 412: When you hear a tone, select either the left ear button 414a or the right ear button 414*b* or use the sensors on your hearing protection device. When the test is complete, in one example, a notification is displayed on the mobile device, as shown in FIG. 4C. For instance, a notification 420 indicates the hearing test is complete, and, in this example, there are no signs of hearing loss.

In one embodiment, the app receives data from both the inner and outer microphones and provides hearing protection notifications to the user. The notifications are, for instance, standard mobile device notifications, texts, emails, etc. Example notifications include: Hearing test is complete and there are no signs of hearing loss; hearing test is complete and there are signs of minor/moderate/significant hearing loss; current hearing test results (e.g., audiograms) compared to previous results; warnings that the microphones have picked up high noise levels for a given amount of time from the environment and selected agencies (e.g., OSHA (Occupational Safety and Health Administration)) suggests hearing loss may occur and that a hearing test should be completed; warnings that the hearing protection device has degraded or is not functioning properly and is not providing the desired hearing protection. Many other examples exist.

In one example, the hearing protection device optionally contains a storage device (e.g., a micro SD card) to save the audiograms and noise levels from the environment. Data could be downloaded periodically for tracking purposes.

Automatic notifications (e.g., emails, texts, etc.) can be generated and sent to users or other subjects (e.g., managers, health services personnel, human resources personnel, selected persons, etc.) for various purposes, including tracking the notifications, managing the user's health, etc.

In one aspect, the speaker is used to generate an active noise cancelling wave inside the hearing protection device to cancel out noise detected on the built-in microphones. This integrates well with existing noise cancelling headphone devices.

Alternatively, in another embodiment, the hearing protection device can communicate with Wi-Fi and/or broadband cellular networks (e.g., 3G, 4G, 5G) in the environment and relay notifications via the built-in speaker to eliminate use of the mobile device. Again, many variations are possible.

Figure 5:
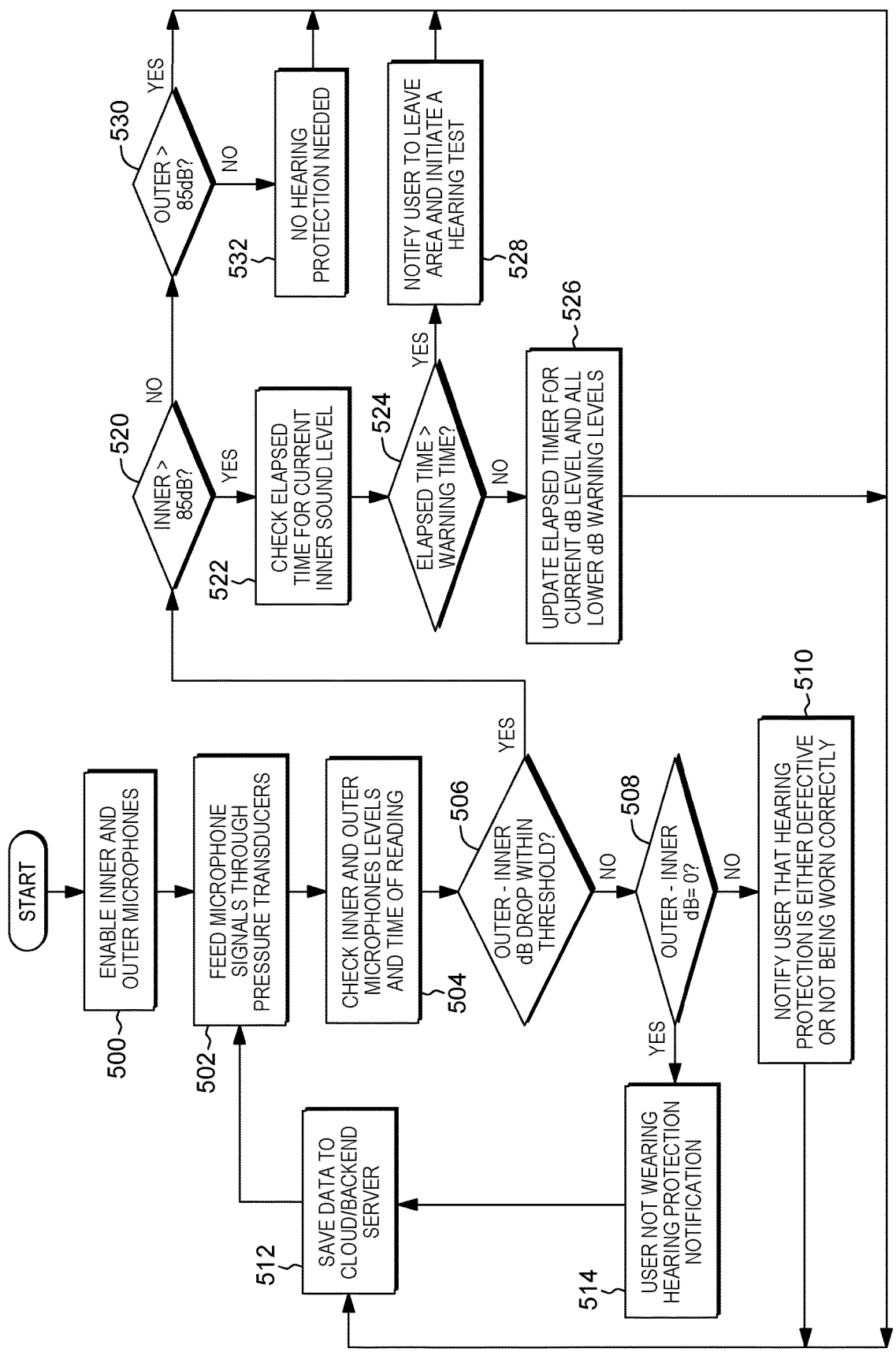
FIG. 5 depicts one example of processing to determine whether on-demand testing is to be performed, in accordance with an aspect of the present invention.

One embodiment of using a hearing protection device to determine, in real-time, whether a hearing test is to be performed, on-demand, is described with reference to FIG. 5. Various components of the hearing protection device to perform one or more functions described in FIG. 5 are described above. Further, one or more functions may be performed, for instance, by one or more processors. One or more of the processors may be included within the hearing protection device (e.g., the various components of the hearing protection device or otherwise) or separate from the hearing protection device.

Referring to FIG. 5, in one embodiment, one or more of inner and outer microphones 104*a*-104*d* are enabled (e.g., turned on), STEP 500. Microphone signals from the enabled microphones are fed through, for instance, pressure transducers of the microphones, STEP 502. A check is made, by for instance, a processor of the hearing protection device (e.g., a processor of one of the components of the device, a processor separate from the components but a part of the device, or a processor coupled to the device) of the inner and outer microphone levels and a time of the reading, STEP 504. A determination is made, by for instance a processor, as to whether a value of the outer microphone level (outer decibel (dB)) minus a value of the inner microphone level (inner decibel) is within a selected threshold, INQUIRY 506. If the outer decibel minus the inner decibel is not within the threshold, then a further determination is made as to whether the outer decibel minus the inner decibel has a predetermined relationship to a predetermined value (e.g., =0), INQUIRY 508. Based on the outer decibel minus the inner decibel not having the predetermined relationship with the predetermined value (e.g., not=0), then in one example, the user is notified that the hearing protection device is defective or not being worn correctly, STEP 510. The data is then saved, e.g., to the cloud or to a backend server, STEP 512, and processing continues at STEP 502.

Returning to INQUIRY 508, if the outer decibel minus the inner decibel has the predetermined relationship with the predetermined value (e.g., =0), then a notification is sent, e.g., to the user or another subject, that the user is not wearing the hearing protection device, STEP 514. In one example, the notification may be sent to one or more mobile devices, laptop computers, desktop computers, tablets, and/or to wearable technology (e.g., a watch), etc. Processing continues with STEP 512.

Returning to INQUIRY 506, if the outer decibel minus the inner decibel is within the threshold, a determination is made as to whether the inner decibel has a predetermined relationship with a selected decibel (e.g., is inner decibel >85 decibels), INQUIRY 520. If the inner decibel has the predetermined relationship with the selected decibel, then a check is made of the elapsed time for the current inner sound level, STEP 522. A determination is made as to whether the elapsed time has a predetermined relationship (e.g., greater than) with a warning time, INQUIRY 524. That is, has the user been exposed to unacceptable noise levels for a period of time, e.g., greater than allowed (e.g., by OSHA or other entities)? If the elapsed time does not have the predetermined relationship with the warning time, then the elapsed time for the current decibel level and the lower decibel warning levels are updated (e.g., by a processor), STEP 526.

Returning to INQUIRY 524, if the elapsed time has the predetermined relationship with the warning time, then, in one example, the user is notified to leave the area and initiate a hearing test, STEP 528. This hearing test, in accordance with an aspect of the present invention, is on-demand in that it is to be performed at the current time (not scheduled for a later day). Processing continues with STEP 512.

Returning to INQUIRY 520, if the inner decibel does not have the predetermined relationship with the selected decibel, then a determination is made as to whether the outer decibel has a predetermined relationship with the selected decibel (e.g., >85 decibels), INQUIRY 530. If the outer decibel does not have the predetermined relationship with the selected decibel, then no hearing protection is needed, STEP 532. In one example, such a notification is provided to the user and/or one or more other subjects. Processing continues with STEP 512.

Returning to INQUIRY 530, if the outer decibel has the predetermined relationship with the selected decibel, then, in one example, no notification is provided, and processing continues with STEP 512.

Further details of performing a hearing test are described with reference to FIG. 6. The test may be performed at any time during a selected time period (e.g., during a work shift). For instance, the test may be performed in the beginning or end of the shift, periodically during the shift, or based on an event, such as a sudden loud noise detected in a microphone of the hearing protection device.

Figure 6:
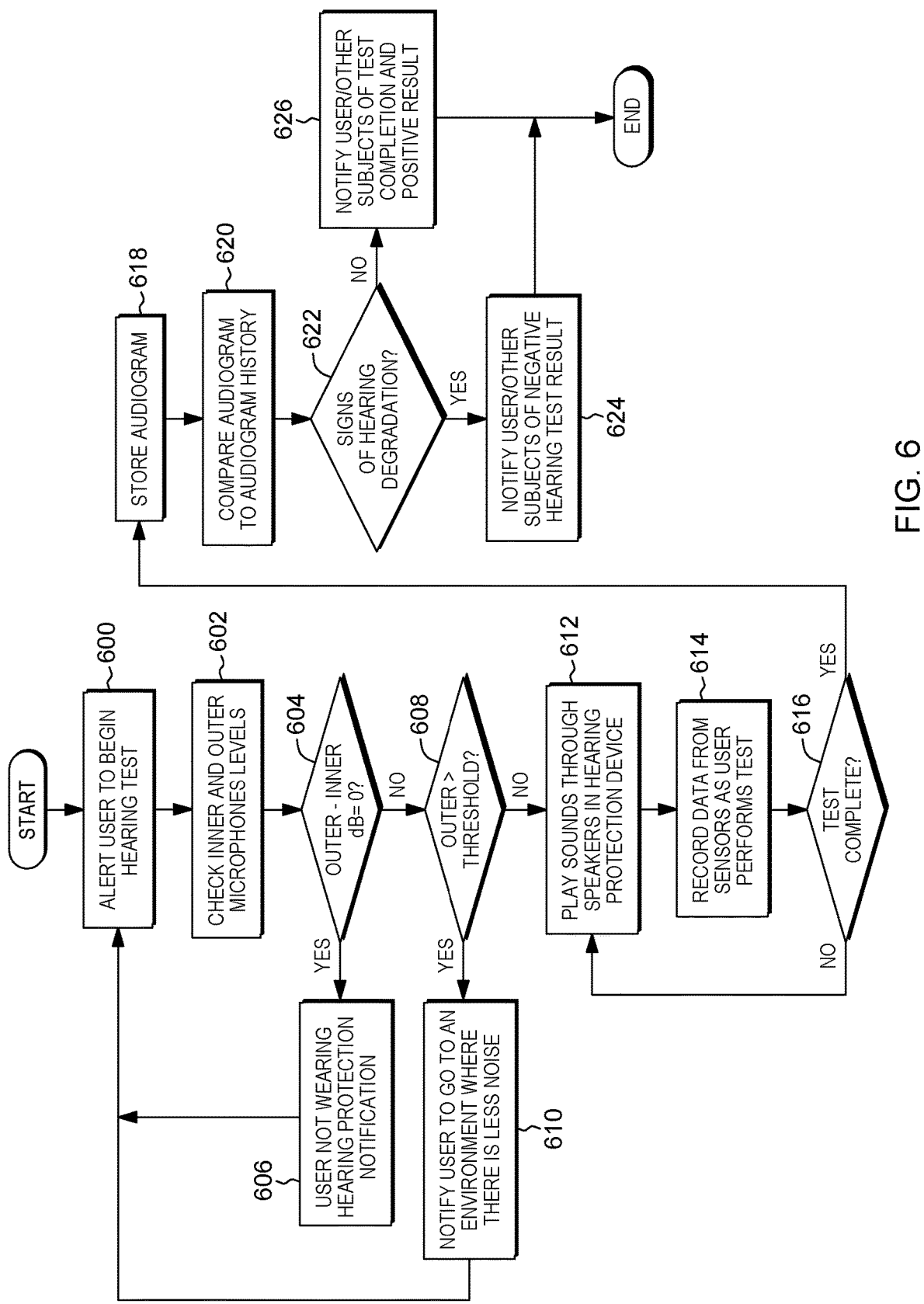
FIG. 6 depicts one example of performing on-demand testing for a detected condition, in accordance with an aspect of the present invention.

Referring to FIG. 6, in one embodiment, a user is alerted to begin a hearing test, STEP 600. As examples, this alert is received at the hearing protection device itself and/or on a select device, such as a mobile phone, other wearable technology, such as a watch, or other devices, etc. Based on the alert, in one embodiment, a determination is made as to whether the environment is suitable for a hearing test (e.g., is it quiet enough?). In one embodiment, a processor is used in making this determination (e.g., a processor in one of the components of the hearing protection device, a processor otherwise within the hearing protection device, or a processor separate from the hearing protection device). To check the noise level of the environment, the inner and outer microphone levels are checked, in one example, STEP 602. A determination is made as to whether the outer decibel minus the inner decibel has a predetermined relationship with a predetermined value (e.g., =0), INQUIRY 604. If the outer decibel minus the inner decibel has the predetermined relationship with the predetermined value, in one example, a notification is provided to, e.g., the user or another subject, that the user is not wearing a hearing protection device, STEP 606. Processing then continues to STEP 600.

Returning to INQUIRY 604, if the outer decibel minus the inner decibel does not have the predetermined relationship with the predetermined value, then a further check is made as to whether the outer decibel has a predetermined relationship (e.g., greater than) with respect to a select threshold, INQUIRY 608. If the outer decibel does have the predetermined relationship with respect to the select threshold, then the user is notified to go to an environment where there is less noise, STEP 610. Processing continues to STEP 600.

Returning to INQUIRY 608, if the outer decibel does not have the predetermined relationship with respect to the select threshold, then in one example, the test begins. Sounds are played through the speakers in the hearing protection device, STEP 612. As the user hears a sound in an ear, in one example, the user presses or otherwise activates a sensor associated with that ear on the hearing protection device to record whether the user heard the sound, STEP 614. In one example, the timing of sounds during the test are to be varied and occasional frequencies are to be played outside of a human hearing range to ensure the user actually took the test.

A determination is made, e.g., by a processor, as to whether the test is complete, INQUIRY 616. If not, then processing continues to STEP 612; otherwise, processing continues to STEP 618, in which, in one example, an audiogram is stored. In one example, an audiogram is generated and stored, along with a timestamp, on, for instance, a user profile and/or a company database. It is used to record the user's hearing over time.

In one embodiment, the audiogram is compared to an audiogram history, STEP 620. A check is made as to whether, based on the comparison, there are signs of hearing degradation for the user over a selected period of time, INQUIRY 622. If there are signs of hearing degradation (above what is expected over time), then the user and/or one or more other subjects are notified of the negative hearing test result, STEP 624. As examples, actions may be taken based on the negative results including, but not limited to, moving away from the noisy area, decreasing the decibel level in the environment, shutting off machinery, slowing down motors, providing notifications, using different hearing protection devices, etc. In one example, thresholds may be used to determine when certain subjects are notified and/or what actions should be taken by the user or others. Further, scheduled periodic tests for this user may be accelerated, so that actions may be taken as quickly as possible to protect the user's hearing. Additionally, in one or more embodiments, the user may be asked to use higher attenuation hearing protection or not to enter a noisy environment (e.g., over a threshold).

Further, in one aspect, the machinery operated by a user is communicatively coupled (e.g., via WiFi, broadband cellular networks, etc.) to the hearing protection device. In one example, the machinery is automatically controlled (e.g., slowed down, certain functions shut off, etc.) based on negative results of a test or a select threshold being met. Alternatively, based on positive results of a test, the functionality of the machinery may be increased (e.g., automatically) to provide increased output from the machinery. Other examples are possible.

Returning to INQUIRY 622, if, however, if there are no signs of hearing degradation, then in one example, the user and/or another subject is notified of test completion and the positive result, STEP 626. Other examples are possible.

In one aspect, results of on-demand tests for selected users may be maintained in a server (e.g., the cloud or a backend server). Further, in one example, certain users may be grouped together. In one embodiment, apps on selected devices of users (e.g., mobile devices, tablets, computers, wearable technology, etc.) are used to provide the tests results or other information to the cloud or backend server, as further described with reference to FIG. 7.

Figure 7:
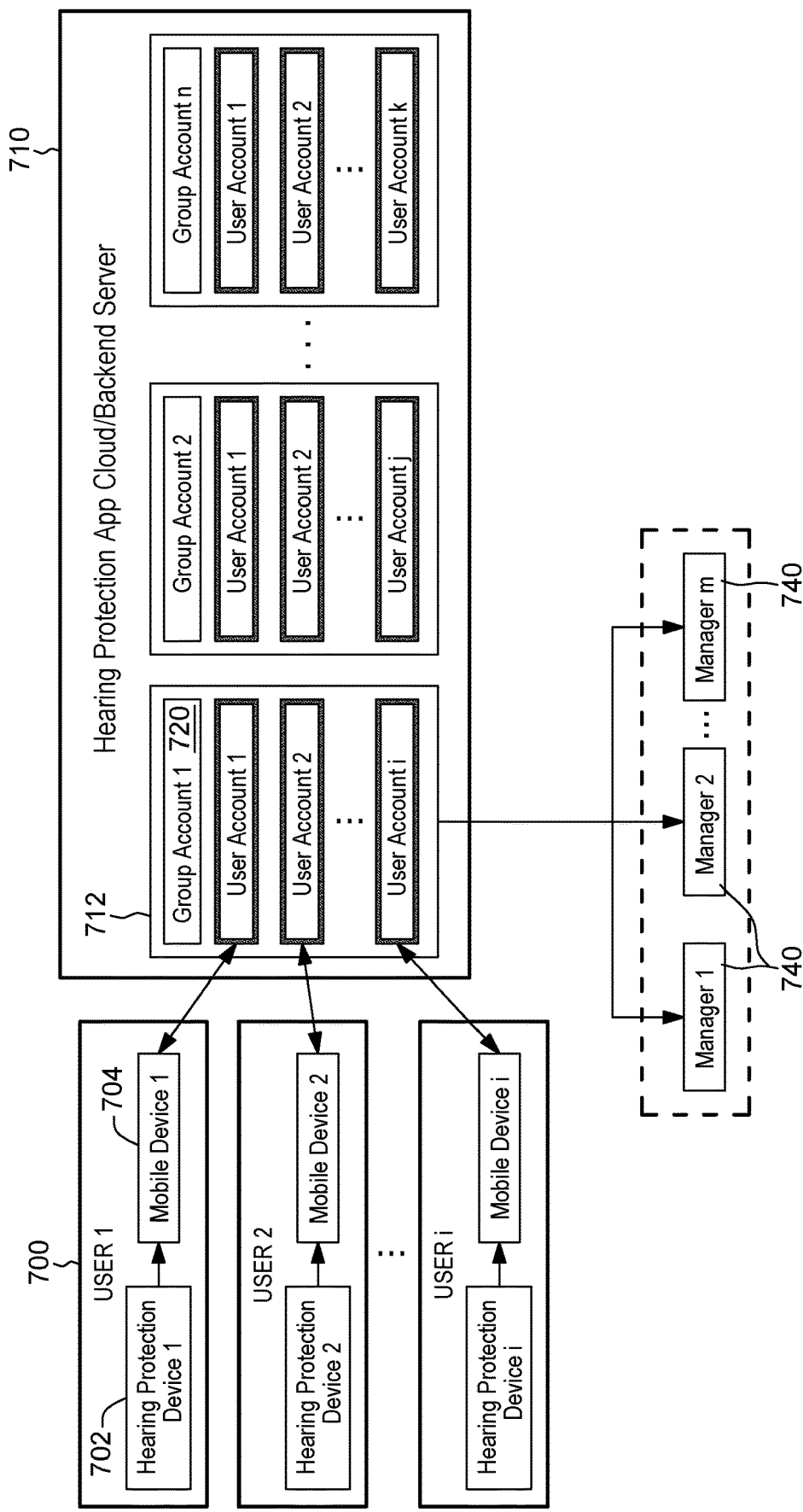
FIG. 7 depicts one example of a network environment using one or more aspects of the present invention.

Referring to FIG. 7, each of a plurality of users 700 uses a hearing protection device 702. Hearing protection device 702 is communicatively coupled to a selected device 704 of the user, such as a mobile device, in this example. In one example, selected device 704 includes an app that receives the tests results and provides the test results and/or other information to one or more servers 710. The one or more servers may be in the cloud or are backend servers, as examples. The tests results and/or other information for individual users are stored in select locations 712 of one or more servers 710.

In one example, the users are grouped based on a selected criterion, and a group account 720 is provided for the group of users. For instance, group account 720 has 1 to i users associated therewith. As an example, the users may be employees of a company and the group account is a company account. Other examples are possible.

Access to a group account 720 may be restricted to certain managing units 740. A managing unit is responsible for one or more aspects of one or more users associated with a particular group. A managing unit includes, for instance, a manager, supervisor, boss, human resources personnel, and/or health services personnel, etc. having responsibility for some aspect of the user (e.g., ensuring the user is performing indicated tests). Access is granted to enable the managing unit to determine, for instance, whether the user is participating in the tests, whether different protection devices are to be used, whether a user has a selected condition (e.g., hearing loss), etc.

In a further embodiment, the mobile device is not used. Instead, a hearing protection device 702 of a user is communicatively coupled to one or more servers 710 (e.g., the cloud or backend server) without the use of, for instance, the mobile device. Test results/information from hearing protection device 702 are provided (e.g., via wireless communication) to a server 710, and stored in a location 712. For instance, test results/information are stored in a group account for the user. One or more managing units 740 have access to one or more of locations 712. Many variations are possible.

In one or more aspects, a device (e.g., a hearing protection device) is used for hearing protection, as well as to perform a test (e.g., a hearing test) on-demand. The device relays notifications to a user and/or another subject in real-time relating to the tests. The notifications may indicate, for instance, that a problem exists (such as hearing loss), that further tests are to be performed, that more suitable protection is needed, that the noise level in the environment is to be reduced, etc. The notifications are relayed via, e.g., a network.

In one example, the network is associated with a workplace and is used to determine the health and safety of employees of the workplace. For instance, in working environments in which noise levels may be high, such as data centers, factories, construction sites or other environments with machinery that may have a high noise level (e.g., above 85 decibels), OSHA requires hearing protection for the workers of that environment. Further, OSHA requires annual hearing tests for users in high noise environments, which may be conducted offsite. However, this time frame may be too long, and users could experience significant hearing damage between tests. Thus, in accordance with an aspect of the present invention, the hearing protection device used to protect the user is also used to detect in real-time a condition that is to be addressed currently, and therefore, initiates an on-demand hearing test. This test may be performed on-site and, in one example, is performed using the hearing protection device.

Figure 8A:
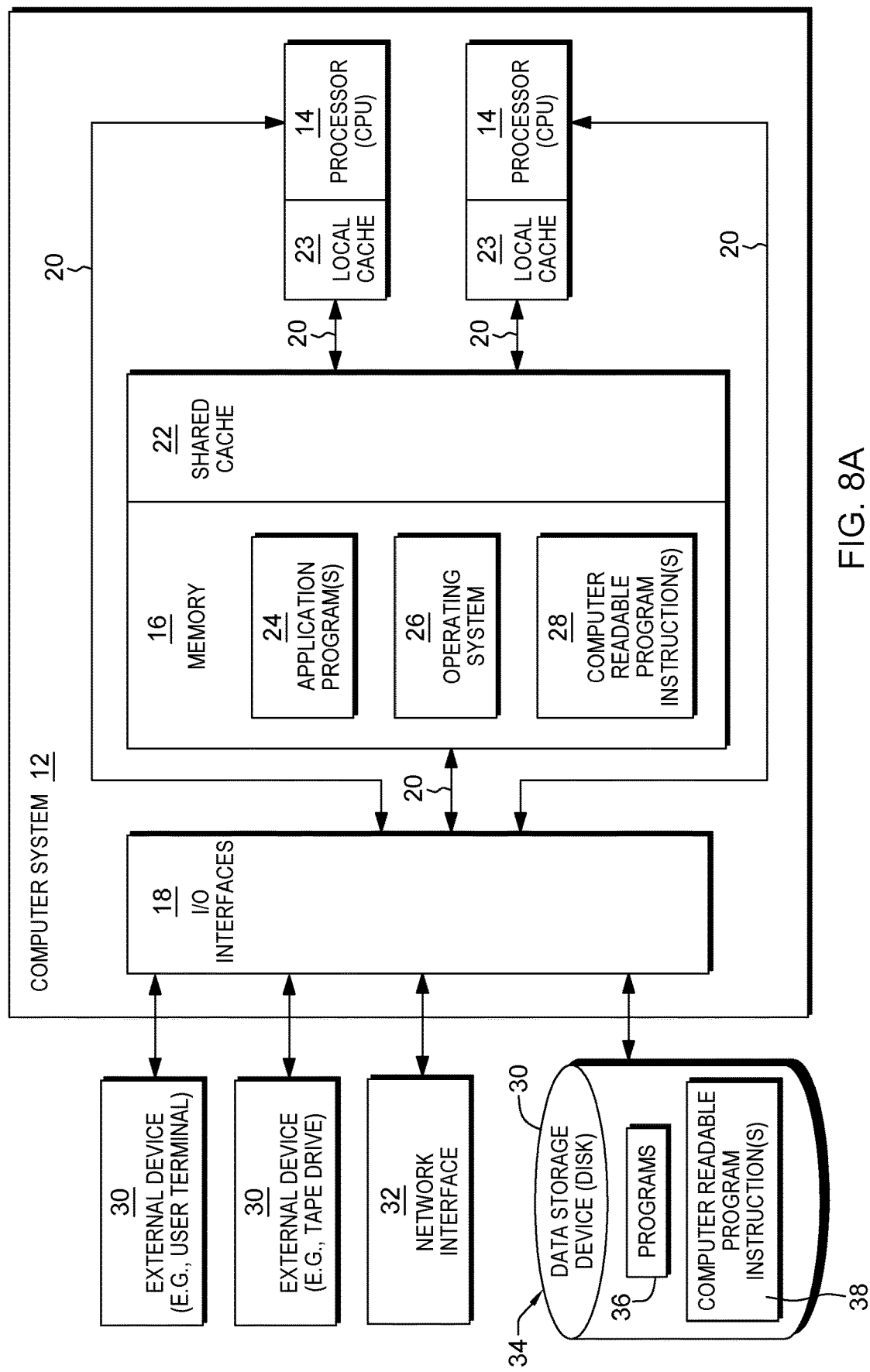
FIG. 8A depicts one example of a computing environment including one or more processors to incorporate and use one or more aspects of the present invention.

As indicated above, processors may be used in various functions relating to on-demand testing, including collecting the data (e.g., noise levels), comparing the data, taking action (e.g., provide notification, initiate testing), etc. Therefore, further details regarding processors that may be used in one or more aspects of the on-demand testing are described with reference to FIG. 8A. Additionally, an example environment that may include one or more of the processors, is described. With reference to FIG. 8A, one example of a computer system that includes processors that may be used by one or more aspects of the present invention is described. In this example, the computer system is part of a computing environment including additional components that may or may not be used by aspects of the present invention.

As shown in FIG. 8A, a computing environment 10 includes, for instance, a computer system 12 shown, e.g., in the form of a general-purpose computing device. Computer system 12 may include, but is not limited to, one or more processors or processing units 14 (e.g., central processing units (CPUs)), a memory 16 (a.k.a., system memory, main memory, main storage, central storage or storage, as examples), and one or more input/output (I/O) interfaces 18, coupled to one another via one or more buses and/or other connections 20.

Bus 20 represents one or more of any of several types of bus structures, including a memory bus or memory controller, a peripheral bus, an accelerated graphics port, and a processor or local bus using any of a variety of bus architectures. By way of example, and not limitation, such architectures include the Industry Standard Architecture (ISA), the Micro Channel Architecture (MCA), the Enhanced ISA (EISA), the Video Electronics Standards Association (VESA) local bus, and the Peripheral Component Interconnect (PCI).

Memory 16 may include, for instance, a cache 22, such as a shared cache, which may be coupled to local caches 23 of processors 14. Further, memory 16 may include one or more programs or applications 24, an operating system 26, and one or more computer readable program instructions 28. Computer readable program instructions 28 may be configured to carry out functions of embodiments of aspects of the invention.

Computer system 12 may also communicate via, e.g., I/O interfaces 18 with one or more external devices 30 and/or one or more network interfaces 32. Example external devices include a user terminal, data storage devices, such as a tape drive, disk or other data storage devices, a pointing device, a display, etc. In one particular example, a data storage device 34 may store one or more programs 36, one or more computer readable program instructions 38, and/or data, etc. The computer readable program instructions may be configured to carry out functions of embodiments of aspects of the invention.

Network interface 32 enables computer system 12 to communicate with one or more networks, such as a local area network (LAN), a general wide area network (WAN), and/or a public network (e.g., the Internet), providing communication with other computing devices or systems.

Computer system 12 may include and/or be coupled to removable/non-removable, volatile/non-volatile computer system storage media. For example, it may include and/or be coupled to a non-removable, non-volatile magnetic media (typically called a "hard drive"), a magnetic disk drive for reading from and writing to a removable, non-volatile magnetic disk (e.g., a "floppy disk"), and/or an optical disk drive for reading from or writing to a removable, non-volatile optical disk, such as a CD-ROM, DVD-ROM or other optical media. It should be understood that other hardware and/or software components could be used in conjunction with computer system 12. Examples, include, but are not limited to: microcode, device drivers, redundant processing units, external disk drive arrays, RAID systems, tape drives, and data archival storage systems, etc.

Computer system 12 may be operational with numerous other general purpose or special purpose computing system environments or configurations. Examples of well-known computing systems, environments, and/or configurations that may be suitable for use with computer system 12 include, but are not limited to, personal computer (PC) systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

In one example, a processor, such as processor 14, may execute one or more components to perform one or more aspects of the present invention. These components may be stored in memory, including main memory (e.g., memory 16) and/or one or more caches (e.g., shared cache 22, local cache 23) and/or external storage (e.g., device 34), and may be executed by one or more processors (e.g., processor 14). Many variations are possible.

Figure 8B:
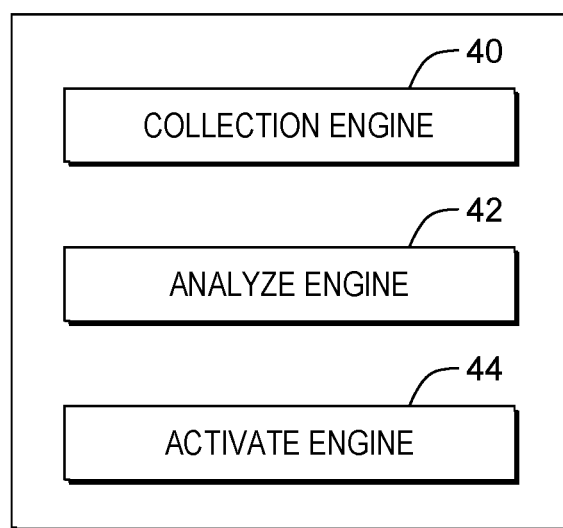
FIG. 8B depicts further details of a processor of FIG. 8A, in accordance with one or more aspects of the present invention.

In one example, referring to FIG. 8B, one or more components of a processor (e.g., processor 14) to perform one or more aspects of the present invention include, for instance, a collection engine 40 to collect information for the users (e.g., from one or more microphones), such as noise levels; an analyze engine 42 to analyze the collected information to determine, for instance, whether testing is to be performed on-demand or if testing has been performed, whether a selected condition exists (e.g., hearing loss); and an activate engine 44 that initiates and/or performs an action, such as initiate a test, provide notification that a test is to be performed, provide notification of results of a test, generate an active noise cancelling wave, control machinery, etc. The components executed by a processor may be individual components or combined in one component. Further, there may be more, fewer and/or different components. Many variations are possible.

In one or more further aspects, personalized data is used to customize a hearing test to a user based on a history of prior hearing tests. Tests can change over time based on both personal data, as well as new information learned from analytics on various users (e.g., more tones can be played in a frequency range in which the user is showing signs of hearing loss, etc.). Moreover, tests may change temporarily. For instance, if a user is subjected to a sudden loud noise that causes temporary hearing loss, tests over the next few days may be suggested more often and tailored towards specific frequencies that may have been affected. Other variations are possible.

Moreover, in a further aspect, analytics are performed across multiple users (e.g., employees) in one or more groups (e.g., companies) in similar and/or different environments to discover trends to better protect users and/or improve standards (e.g., hearing protection standards). For instance, cognitive analytics are used, in one embodiment, on long term data among different types of employees in different work areas to discover trends that could help improve hearing protection and the way in which hearing protection is used. Based on the trends, actions may be taken to reduce the noise or provide more suitable hearing protection devices, as examples. Other possibilities also exist.

To perform the analytics, in one example, a system such as a Watson™ system (offered by International Business Machines Corporation; Watson and IBM Watson are trademarks or registered trademarks of International Business Machines Corporation in at least one jurisdiction) could perform the analytics on the cloud/backend server with data from many different users in different environments to discover trends and use those discoveries to feed useful data back to standard agencies (e.g., OSHA), employers and/or users of the hearing protection devices to ensure that they are best protected against hearing loss.

In one or more aspects, machine learning is used. As examples, machine learning is used to detect whether a test is to be performed, determine whether a selected condition may exist now or in the future, and/or to learn trends. Machine learning algorithms generate and train algorithms to create a model utilized to detect a selected condition. For instance, in an initialization stage, program code (e.g., hardware and/or software) trains these algorithms, based on patterns for a given user (and/or across all users with certain shared attributes). A machine learning training system may be utilized, in one or more aspects, to perform cognitive analyses of various inputs, including sensed data, historical data, result data and/or other data. Training data utilized to train the model in one or more embodiments of the present invention includes, for instance, data that is personalized to the user, including but not limited to, age, health, hearing range, etc. The program code in embodiments of the present invention performs a cognitive analysis to generate data structures, including algorithms utilized by the program code to predict states of a given user. Machine learning (ML) solves problems that are not solved with numerical means alone. In this ML-based example, program code extracts various features/attributes from ML training data, which may be resident in one or more databases comprising user-related data and general data. Features are utilized to develop a predictor function, $h(x)$, also referred to as a hypothesis, which the program code utilizes as a machine learning model.

In identifying various user states and/or behaviors indicative of states in the ML training data, the program code can utilize various techniques including, but not limited to, mutual information, which is an example of a technique that can be utilized to identify features in an embodiment of the present invention. Further embodiments of the present invention utilize varying techniques to select features (elements, patterns, attributes, etc.), including but not limited to, diffusion mapping, principal component analysis, recursive feature elimination (a brute force approach to selecting features), and/or a Random Forest, to select the attributes related to various user states. The program code may utilize a machine learning algorithm to train the machine learning model (e.g., the algorithms utilized by the program code), including providing weights for the conclusions, so that the program code can train the predictor functions that comprise the machine learning model. The conclusions may be evaluated by a quality metric. By selecting a diverse set of ML training data, the program code trains the machine learning model to identify and weight various attributes (e.g., features, patterns) that correlate to various states of a user.

The model generated by the program code is self-learning as the program code updates the model based on active user feedback received from users, as well as from the feedback received from data related to monitoring the user. For example, when the program code determines that there is a potential problem at a given time that was not previously predicted by the model, the program code alerts the user, but also, utilizes a learning agent to update the model to reflect the state of the user, in order to improve predictions in the future. Additionally, when the program code determines that a prediction is incorrect, either based on receiving user feedback through an interface or based on continuously monitoring the user, the program code updates the model to reflect the inaccuracy of the prediction for the given period of time. Program code comprising a learning agent cognitively analyzes the data deviating from the modeled expectations and adjusts the model in order to increase the accuracy of the model, moving forward.

In one or more embodiments, program code executing on one or more processors, utilizes an existing cognitive analysis tool or agent to tune the model, based on data obtained from the various data sources, including sensor data. One or more embodiments utilize an IBM Watson® system as the cognitive agent. In one or more embodiments, the program code interfaces with IBM Watson application programming interfaces (APIs) to perform a cognitive analysis of obtained data.

In one or more embodiments, the program code trains aspects of the IBM Watson Application Program Interface (API) to learn the relationships between physiological elements from the sensors and the patterns of the user. Utilizing an existing cognitive agent, such as an IBM Watson system, expands the type of user data that the program code can integrate into the model. For example, sensor data can include documentary, visual, and audio data, which the program code can process, based on its utilization of an IBM Watson system. Specifically, in one or more embodiments, certain of the APIs of the IBM Watson API comprise a cognitive agent (e.g., learning agent) that includes one or more programs, including, but not limited to, natural language classifiers, Retrieve and Rank (i.e., a service available through the IBM Watson Developer Cloud that can surface the most relevant information from a collection of documents), concepts/visual insights, trade off analytics, document conversion, and/or relationship extraction. In an embodiment, one or more programs analyze the data obtained by the program code across various sources utilizing one or more of a natural language classifier, retrieve and rank APIs, and trade off analytics APIs. The IBM Watson Application Program Interface (API) can also provide audio related API services, in the event that the collected data includes audio, which can be utilized by the program code, including but not limited to natural language processing, text to speech capabilities, and/or translation.

In generating and updating the model, the program code can segment future periods into distinct portions, in order to provide users with a usable guide for anticipating the state of a user. In one or more embodiments, the program code divides each twenty-four (24) hour period into defined time segments of a certain length (e.g., twenty (20) minutes). The program code can generate an average state prediction for each distinct period, for example, by synthesizing or averaging the data (e.g., sensor data) over each time segment.

The program code can provide state predictions and/or alerts for a given user as varying values. In one or more embodiments, the program code calculates a binary injury value for the user, which the program code provides to users (e.g., subscribers). Thus, in one or more embodiments, the program code indicates to a user whether an injury (e.g., hearing loss) is predicted for a given user. In one or more embodiments, should the user behavior deviate from the model predictions, based on continuously monitoring the user (e.g., utilizing IoT devices and other computing devices including environmental and/or personal sensors), the program code can immediately alert users, for example, when a potential injury is detected.

In one or more embodiments, the program code utilizes a neural network to analyze user-related data to generate the model utilized to predict the state of a given user at a given time. Neural networks are a biologically-inspired programming paradigm which enable a computer to learn from observational data, in this case, sensor data, and/or other data. This learning is referred to as deep learning, which is a set of techniques for learning in neural networks. Neural networks, including modular neural networks, are capable of pattern (e.g., state) recognition with speed, accuracy, and efficiency, in situations where data sets are multiple and expansive, including across a distributed network, including but not limited to, cloud computing systems. Modern neural networks are non-linear statistical data modeling tools. They are usually used to model complex relationships between inputs and outputs or to identify patterns (e.g., states) in data (i.e., neural networks are non-linear statistical data modeling or decision making tools). In general, program code utilizing neural networks can model complex relationships between inputs and outputs and identify patterns in data. Because of the speed and efficiency of neural networks, especially when parsing multiple complex data sets, neural networks and deep learning provide solutions to many problems in multiple source processing, which the program code in one or more embodiments accomplishes when obtaining data and generating a model for predicting states of a given user during particular intervals (e.g., during particular movements).

One or more embodiments may utilize a neural network (NN) to predict future states of a given user. Utilizing the neural network, the program code can predict the likelihood of the user being in a given state at a subsequent time. The program code obtains (or derives) data related to the user from various sources to generate an array of values (possible states) to input into input neurons of the NN. Responsive to these inputs, the output neurons of the NN produce an array that includes the predicted states. The program code can automatically transmit notifications related to the predicted states based on the perceived validity.

In one or more embodiments, a neuromorphic processor or trained neuromorphic chip can be incorporated into the computing resources executing the program code. One example of a trained neuromorphic chip that is utilized in an embodiment of the present invention is a TrueNorth chip, produced by International Business Machines Corporation.

The TrueNorth chip, also referred to as TrueNorth, is a neuromorphic complementary metal-oxide-semiconductor (CMOS) chip. TrueNorth includes a manycore network on a chip design (e.g., 4096 cores), each one simulating programmable silicon "neurons" (e.g., 256 programs) for a total of just over a million neurons. In turn, each neuron has 256 programmable synapses that convey the signals between them. Hence, the total number of programmable synapses is just over 268 million ($2^{28}$). Memory, computation, and communication are handled in each of the 4096 neurosynaptic cores, so TrueNorth circumvents the von-Neumann-architecture bottlenecks and is very energy-efficient.

One or more aspects of the present invention are inextricably tied to computing and improve technical fields of on-demand testing, injury prevention (e.g., prevention of hearing loss) and/or machine learning, as examples. Technological improvements are provided in real-time, on-demand testing to detect certain conditions.

As described herein, in one or more aspects, a hearing protection device is used in monitoring an environment, initiate on-demand hearing tests, and/or perform the hearing tests. Data from one or more hearing tests and/or the hearing protection device (e.g., the microphones) are used, for instance: to determine if a user's hearing is degrading over time or due to a single incident; and/or to determine if the hearing protection device being used is doing a sufficient job to protect the users or if the user is to have more hearing protection.

Users of many environments may use the hearing protection device and/or one or more aspects of the present invention including, but not limited to, users in data centers, factories, construction; users that use or ride heavy equipment, such as lawn mowers, motorcycles, etc. Many other environments and/or users may benefit from one or more aspects of the present invention.

Although many examples and embodiments are provided herein, other variations and embodiments are possible.

One or more aspects may relate to cloud computing.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 9:
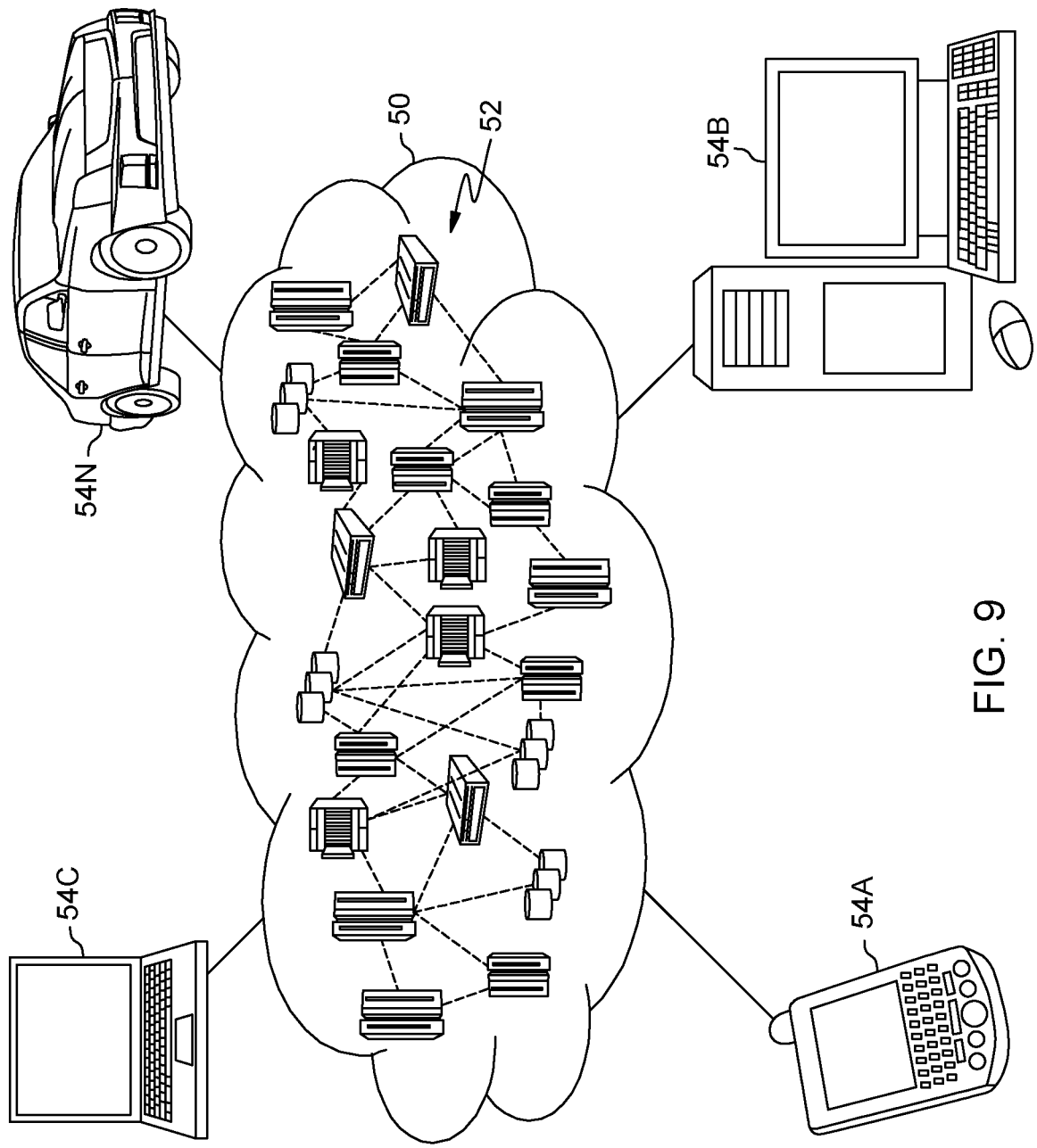
FIG. 9 depicts one embodiment of a cloud computing environment.

Referring now to FIG. 9, illustrative cloud computing environment 50 is depicted. As shown, cloud computing environment 50 comprises one or more cloud computing nodes 52 with which local computing devices used by cloud consumers, such as, for example, personal digital assistant (PDA) or cellular telephone 54A, desktop computer 54B, laptop computer 54C, and/or automobile computer system 54N may communicate. Nodes 52 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 9 are intended to be illustrative only and that computing nodes 52 and cloud computing environment 50 can communicate with any type of computerized device over any type of network and/or network addressable connection (e.g., using a web browser).

Figure 10:
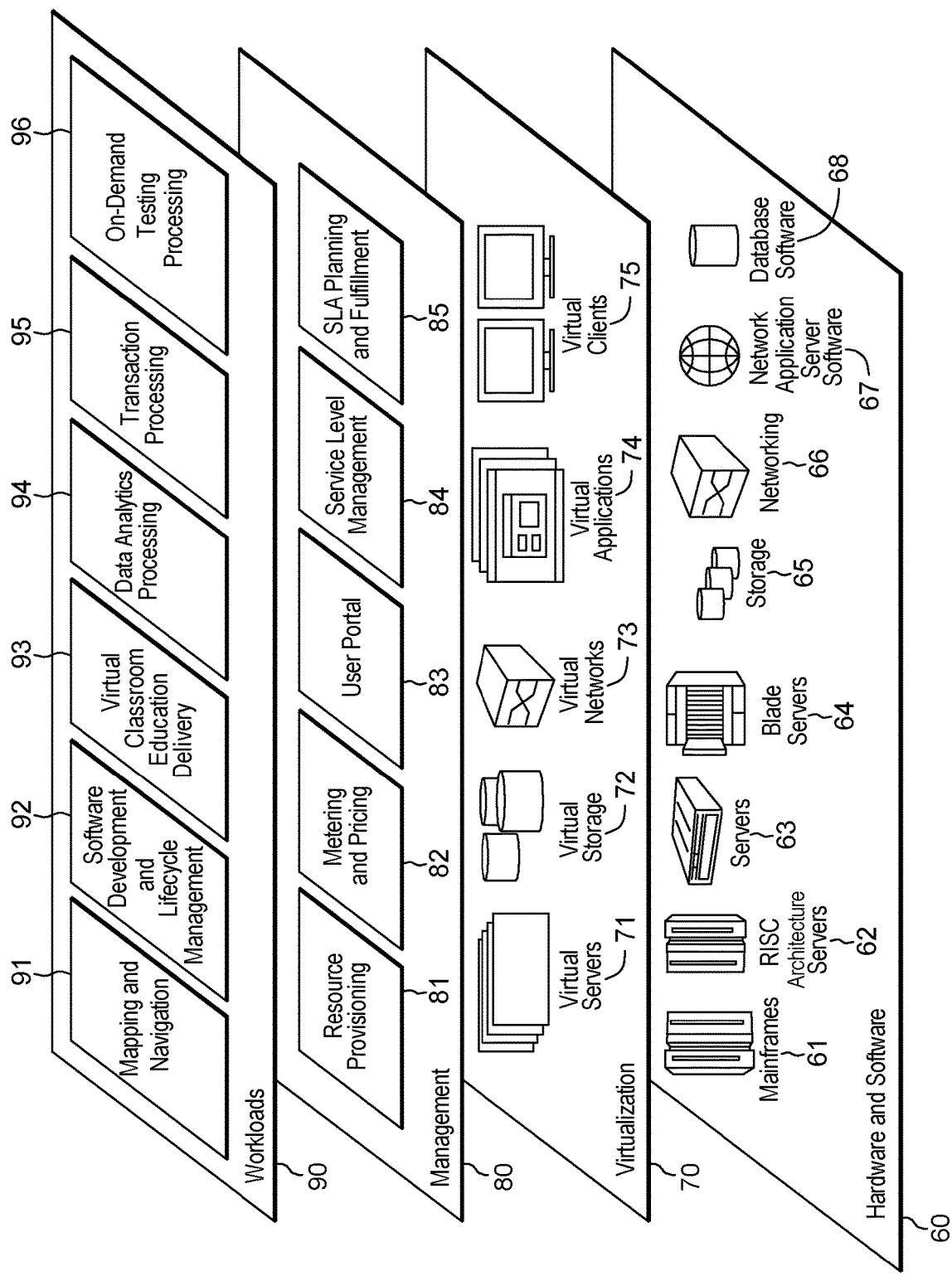
FIG. 10 depicts one example of abstraction model layers.

Referring now to FIG. 10, a set of functional abstraction layers provided by cloud computing environment 50 (FIG. 9) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 60 includes hardware and software components. Examples of hardware components include mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides iduser verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and on-demand testing processing 96.

Aspects of the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In addition to the above, one or more aspects may be provided, offered, deployed, managed, serviced, etc. by a service provider who offers management of customer environments. For instance, the service provider can create, maintain, support, etc. computer code and/or a computer infrastructure that performs one or more aspects for one or more customers. In return, the service provider may receive payment from the customer under a subscription and/or fee agreement, as examples. Additionally or alternatively, the service provider may receive payment from the sale of advertising content to one or more third parties.

In one aspect, an application may be deployed for performing one or more embodiments. As one example, the deploying of an application comprises providing computer infrastructure operable to perform one or more embodiments.

As a further aspect, a computing infrastructure may be deployed comprising integrating computer readable code into a computing system, in which the code in combination with the computing system is capable of performing one or more embodiments.

As yet a further aspect, a process for integrating computing infrastructure comprising integrating computer readable code into a computer system may be provided. The computer system comprises a computer readable medium, in which the computer medium comprises one or more embodiments. The code in combination with the computer system is capable of performing one or more embodiments.

Although various embodiments are described above, these are only examples. For example, other types of devices, sensors and/or components, etc. may be used in one or more embodiments. Many variations are possible.

Further, other types of computing environments can benefit and be used. As an example, a data processing system suitable for storing and/or executing program code is usable that includes at least two processors coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed is:

1. A method of facilitating testing, said method comprising:
    monitoring, using a device, one or more environment conditions of an environment in which a user is located, the monitoring being performed in real-time;
    detecting by the device, based on the monitoring, an alert condition relating to the environment representative of a potentially damaging noise level in the environment in which the user is located;
    based on detecting the alert condition representative of the potentially damaging noise level, initiating on-demand testing of a sensory component of the user, the on-demand testing to test for a selected condition relating to health of the user at the time the user is notified that testing is to be performed.

2. The method of claim 1, wherein the device comprises a wearable device.

3. The method of claim 2, wherein the wearable device comprises a hearing protection device.

4. The method of claim 3, wherein the monitoring comprises using one or more microphones of the hearing protection device to determine a noise level within the environment, the noise level being an environment condition.

5. The method of claim 1, wherein the alert condition comprises a noise level in the environment above a certain value.

6. The method of claim 1, wherein the initiating comprises sending a notification by the device, based on the alert condition, indicating a test is to be performed on-demand.

7. The method of claim 6, further comprising performing the test, on-demand, based on the notification.

8. The method of claim 7, further comprising saving results of the test, the results to be used in analytics to determine whether one or more changes are to be made to the environment or the device.

9. The method of claim 7, wherein the performing the test comprises performing the test using the device.

10. The method of claim 7, wherein the device comprises a hearing protection device, and wherein the performing the test comprises performing a hearing test using the hearing protection device, based on the alert condition comprising a noise level above a certain value.

11. The method of claim 7, further comprising automatically adjusting a machine of the environment contributing to the alert condition representative of the potentially damaging noise, based on results of the test, the machine being separate from the device, and the automatically adjusting reducing the potentially damaging noise level in the environment in which the user is located.

12. A system for facilitating testing, said system comprising:
  a device configured to perform a method, the method comprising:
    monitoring, using the device, one or more environment conditions of an environment in which a user is located, the monitoring being performed in real-time;
    detecting by the device, based on the monitoring, an alert condition relating to the environment representative of a potentially damaging noise level in the environment in which the user is located;
    based on detecting the alert condition representative of the potentially damaging noise level, initiating on-demand testing of a sensory component of the user, the on-demand testing to test for a selected condition relating to health of the user at the time the user is notified that testing is to be performed.

13. The system of claim 12, wherein the device comprises a hearing protection device, and the monitoring comprises using one or more microphones of the hearing protection device to determine a noise level within the environment, the noise level being an environment condition.

14. The system of claim 12, wherein the initiating comprises sending a notification by the device, based on the alert condition, indicating a test is to be performed on-demand.

15. The system of claim 14, wherein the method further comprises performing the test, on-demand, based on the notification.

16. The system of claim 15, wherein the device comprises a hearing protection device, and wherein the performing the test comprises performing a hearing test using the hearing protection device, based on the alert condition comprising a noise level above a certain value.

17. The system of claim 15, wherein the method further comprises automatically adjusting a machine of the environment contributing to the alert condition representative of the potentially damaging noise, based on results of the test, the machine being separate from the device, and the automatically adjusting reducing the potentially damaging noise level in the environment in which the user is located.

18. A computer program product for facilitating testing, said computer program product comprising:
  a computer readable storage medium readable by a processing circuit and storing instructions for performing a method comprising:
    monitoring, using a device, one or more environment conditions of an environment in which a user is located, the monitoring being performed in real-time;
    detecting by the device, based on the monitoring, an alert condition relating to the environment representative of a potentially damaging noise level in the environment in which the user is located;
    based on detecting the alert condition representative of the potentially damaging noise level, initiating on-demand testing of a sensory component of the user, the on-demand testing to test for a selected condition relating to health of the user at the time the user is notified that testing is to be performed.

19. The computer program product of claim 18, wherein the initiating comprises sending a notification by the device, based on the alert condition, indicating a test is to be performed on-demand.

20. The computer program product of claim 19, wherein the method further comprises performing the test, on-demand, based on the notification, and automatically adjusting a machine of the environment contributing to the alert condition representative of the potentially damaging noise, based on results of the test, the machine being separate from the device, and the automatically adjusting reducing the potentially damaging noise level in the environment in which the user is located.

* * * * *